(12) United States Patent
Matsui et al.

(10) Patent No.: US 10,441,032 B2
(45) Date of Patent: Oct. 15, 2019

(54) METHOD OF MANUFACTURING A SHOE INSOLE

(71) Applicant: KOBE SOGU SEISAKUSHO CO., LTD., Ashiya-shi, Hyogo (JP)

(72) Inventors: Nobuzo Matsui, Ashiya (JP); Yoshiaki Azuma, Ashiya (JP); Moonsik Chung, Ashiya (JP)

(73) Assignee: KOBE SOGU SEISAKUSHO CO., LTD., Ashiya-shi, Hyogo (JP)

( * ) Notice: Subject to any disclaimer, the term of this patent is extended or adjusted under 35 U.S.C. 154(b) by 354 days.

(21) Appl. No.: 14/899,535

(22) PCT Filed: Jun. 12, 2014

(86) PCT No.: PCT/JP2014/003144
§ 371 (c)(1),
(2) Date: Dec. 17, 2015

(87) PCT Pub. No.: WO2014/203506
PCT Pub. Date: Dec. 24, 2014

(65) Prior Publication Data
US 2016/0213094 A1    Jul. 28, 2016

(30) Foreign Application Priority Data

Jun. 18, 2013 (JP) ................................. 2013-127395

(51) Int. Cl.
*A43D 8/00* (2006.01)
*A43B 17/00* (2006.01)
(Continued)

(52) U.S. Cl.
CPC ............ *A43B 17/006* (2013.01); *A43B 7/141* (2013.01); *A43B 7/144* (2013.01); *A43B 7/1415* (2013.01);
(Continued)

(58) Field of Classification Search
CPC ..... A43B 17/006; A43B 7/141; A43B 7/1415; A43B 7/1425; A43B 7/1435; A43B 7/144;
(Continued)

(56) References Cited

U.S. PATENT DOCUMENTS 2,600,864 A * 6/1952 Fuller ................... A43B 7/1415
2/239
4,669,142 A * 6/1987 Meyer ...................... A43B 7/28
12/142 N
(Continued)

FOREIGN PATENT DOCUMENTS

GB         2237972 A   *   5/1991    ............... A43B 7/28
JP         10-327905       12/1998
(Continued)

OTHER PUBLICATIONS

International Search Report and Written Opinion for PCT/JP2014/003144, dated Oct. 14, 2014.
(Continued)

*Primary Examiner* — Jameson D Collier
(74) *Attorney, Agent, or Firm* — Marshall, Gerstein & Borun LLP

(57) ABSTRACT

A method of manufacturing a shoe insole includes an upper cover layer and a lower cover layer conforming in shape to the inner bottom of the shoe, and an insole body retained between the upper cover layer and the lower cover layer, taking a foot sole form to which pads are applied to selected regions of a sole taking a foot sole form; manufacturing an insole frame having a shape conforming to a three-dimensional shape of the foot sole form and applying insole pads to an upper surface of the insole frame, based on positions of marks of the test pads of the foot sole form to which the
(Continued)

pads are applied, wherein the insole body includes the insole frame to which the insole pads are applied.

6 Claims, 6 Drawing Sheets

(51) Int. Cl.
    *A43B 7/28*     (2006.01)
    *A43B 7/14*     (2006.01)
    *A43B 7/24*     (2006.01)
    *A43B 13/12*     (2006.01)
    *A43D 1/02*     (2006.01)
    *A61B 5/107*     (2006.01)
    *A61B 5/1174*     (2016.01)
    *A43B 13/38*     (2006.01)

(52) U.S. Cl.
    CPC .......... *A43B 7/1425* (2013.01); *A43B 7/1435* (2013.01); *A43B 7/1465* (2013.01); *A43B 7/24* (2013.01); *A43B 7/28* (2013.01); *A43B 13/12* (2013.01); *A43B 13/386* (2013.01); *A43B 17/00* (2013.01); *A43D 1/022* (2013.01); *A61B 5/1074* (2013.01); *A61B 5/1174* (2013.01)

(58) Field of Classification Search
    CPC .......... A43B 7/1465; A43B 7/24; A43B 7/28; A43B 13/12; A43B 13/386; A43B 17/00; A43D 1/022; A61B 5/1074; A61B 5/1174
    USPC ........................................... 12/146 B, 146 M
    See application file for complete search history.

(56) References Cited

U.S. PATENT DOCUMENTS

| | | | | |
|---|---|---|---|---|
| 4,756,096 A | * | 7/1988 | Meyer | A43B 7/28 12/142 N |
| 5,787,608 A | * | 8/1998 | Greenawalt | A43B 3/128 36/11.5 |
| 6,195,917 B1 | * | 3/2001 | Dieckhaus | A43B 7/141 36/154 |
| 7,264,604 B1 | * | 9/2007 | Schuren | A43B 7/1425 602/23 |
| 7,594,346 B2 | * | 9/2009 | Dananberg | A43B 7/14 36/174 |
| 8,800,168 B1 | * | 8/2014 | Propet | A43B 7/141 36/173 |
| 2011/0288446 A1 | * | 11/2011 | Hsieh | A43B 1/0081 600/592 |
| 2014/0068967 A1 | * | 3/2014 | Jones | A43B 7/145 36/43 |

FOREIGN PATENT DOCUMENTS

| | | |
|---|---|---|
| JP | 2000-62046 | 2/2000 |
| JP | 2003-088405 A | 3/2003 |
| JP | 2008-048863 A | 3/2008 |

OTHER PUBLICATIONS

International Preliminary Report on Patentability for PCT/JP2014/003144, dated Dec. 22, 2015.

* cited by examiner

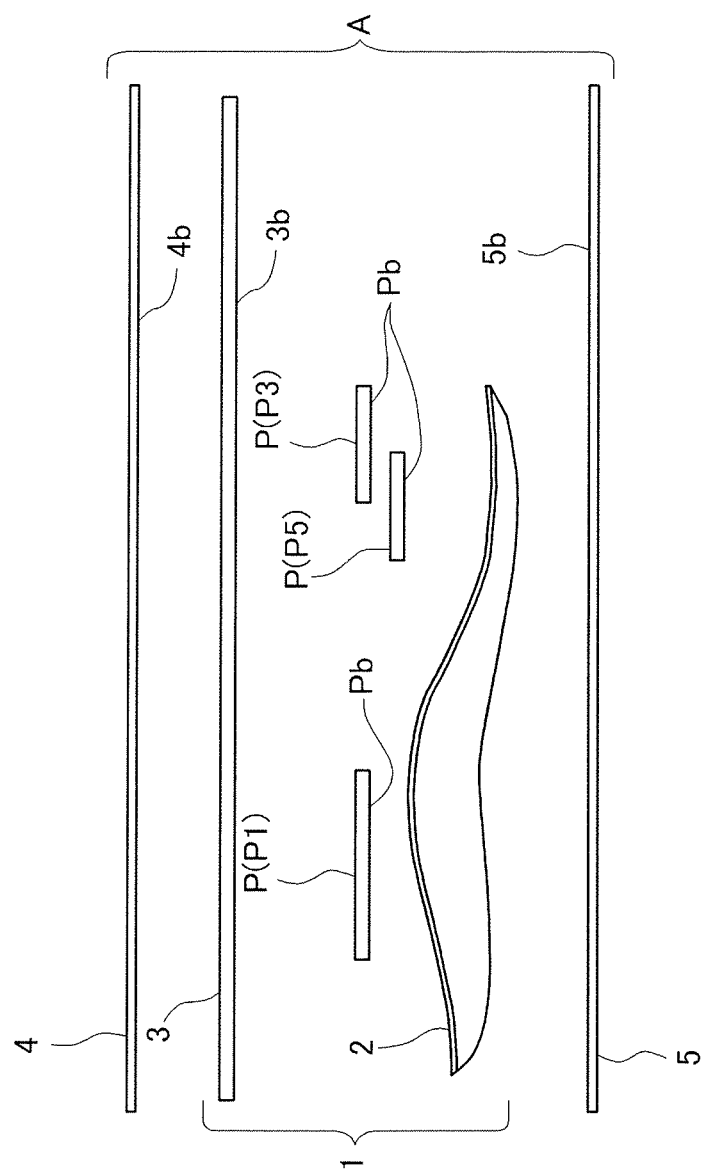

METHOD OF MANUFACTURING A SHOE INSOLE

TECHNICAL FIELD

The present invention relates to a method of manufacturing a shoe insole.

BACKGROUND ART

The sole of a human foot is formed with a transverse arch, a medial longitudinal arch, and a lateral longitudinal arch. If the skeleton of the foot constituting these arches loses its shape, body parts such as the foot, a knee, a waist, a back, a shoulder, and the like get distorted, or become painful, which may lead to a failure in the body. This is well known. The use of a shoe insole appropriate for the foot of a user in a shoe is helpful in preventing such problems.

For example, Patent Literatures 1 and 2 disclose a shoe insole having an arch support function. Patent Literature 1 discloses that a shoe insole is manufactured in such a manner that first to three pads are attached onto an insole body plate to correspond to three arches, respectively, and a cover sheet is applied to the insole body plate attached with the three pads, from an upper side.

Patent Literature 2 describes that since the size, shape and the like of the human foot are varied from person to person, it is difficult to select or manufacture the first to third pads with sizes and shapes which are appropriate for the user of the shoe insole and to place these pads in correct positions, in the configuration of Patent Literature 1.

Patent Literature 2 discloses a manufacturing method of a shoe insole including an upper plate and a lower plate which constitute a sole (foot bottom) plate and are placed to be vertically adjacent to each other, in which a mixture of a base compound and a curing agent of two-pack liquid silicon rubber is placed on the upper surface of the lower plate in positions which substantially correspond to the arches of the sole of the foot, respectively, the user pushes the upper plate with a pressure with the sole of the foot, from an upper side, in a state in which the upper plate overlaps with the lower plate, and thus the silicon rubber is molded and cured to conform to the shapes of the arches.

CITATION LIST

Patent Literature

Patent Literature 1: Japanese-Laid Open Patent Application Publication No. 2003-88405
Patent Literature 2: Japanese-Laid Open Patent Application Publication No. 2008-48863

SUMMARY OF INVENTION

Technical Problem

Patent Literature 2 discloses that the hardness, thickness and size of the two-pack liquid silicon rubber, after being cured, can be adjusted, by changing the kind and/or amount of the curing agent of the two-pack liquid silicon rubber, and therefore an arch support body according to the preference or handicap of the user can be easily manufactured.

However, it can be presumed that it is difficult to adjust the hardness, thickness and size of the two-pack liquid silicon rubber, after being cured so that they are appropriate for the user. Also, whether or not the shoe insole manufactured in the above-described manner is appropriate for the user can be judged only when an expert such as a physical therapist or a prosthetist observes the actual use state of the shoe insole. In other words, even in the manufacturing method disclosed in Patent Literature 2, it is difficult to manufacture the shoe insole which is appropriate for the foot of the user and is effective to the correction or the like of the sole of the foot of the user.

The present invention has been made to solve the above-described problem, and an object is to provide a method of manufacturing a shoe insole, which can manufacture the shoe insole which is appropriate for the foot of the user and is effective to the correction or the like of the sole of the foot.

Solution to Problem

To achieve the above-described object, according to an aspect of the present invention, there is provided a method of manufacturing a shoe insole including an upper cover layer conforming in shape to an inner bottom of a shoe, a lower cover layer conforming in shape to the inner bottom of the shoe, and an insole body retained between the upper cover layer and the lower cover layer, the method comprising: taking a foot sole form to which pads are applied, the foot sole form being a foot sole form to which test pads are applied to selected regions of a sole of a bare foot of a user which uses the shoe insole; taking a foot sole form of the bare foot of the user; manufacturing an insole frame having a shape conforming to a three-dimensional shape of the foot sole form of the bare foot; and applying insole pads having the same shapes as shapes of the test pads, to an upper surface of the insole frame, based on positions of marks of the test pads of the foot sole form to which the pads are applied, wherein the insole body includes the insole frame to which the insole pads are applied.

In accordance with this manufacturing method, an expert such as a physical therapist or a prosthetist determines the regions to which the test pads are applied, which are appropriate for the user, and applies the insole pads having the same shapes as those of the test pads to the upper surface of the insole frame, based on the marks of the test pads of the taken foot sole form to which the pads are applied, and thus the insole pads are placed in the positions appropriate for the user. By taking the foot sole form to which the pads are applied, the insole pads can be placed in correct positions. As a result, it becomes possible to manufacture the shoe insole which is appropriate for the foot of the user and is effective to the correction or the like of the sole of the foot of the user. The taken foot sole form to which the pads are applied may be the foot sole form comprising three-dimensional data (three-dimensional shape data) of the sole of the foot to which the test pads are applied. In the same manner, the foot sole form of the bare foot may be a foot sole form comprising three-dimensional data (three-dimensional shape data) of the sole of the bare foot.

The insole frame may be manufactured to have a shape in which a specified region being close to tiptoes and including a region corresponding to toes is missing, and the method may further comprise: providing a buffering layer on the upper surface of the insole frame to which the insole pads are applied, the buffering layer conforming in shape to the inner bottom of the shoe, wherein the insole body may include the insole frame to which the insole pads are applied, and the buffering layer.

By using the shoe insole manufactured by this manufacturing method, a portion of the insole frame, corresponding to the toes, is missing. This makes it possible to reduce a pressure to the toes in a state in which the user is wearing the shoe.

Each of the foot sole form of the bare foot and the foot sole form to which the pads are applied may be taken by causing the user to push a foot sole form sponge with the sole of the foot and move over out of the foot sole form sponge.

The foot sole form taken by causing the user to push the foot sole form sponge with the sole of the foot and move over out of the foot sole form sponge, may be a foot sole form in, for example, a state in which the user is walking. The reason is as follows. A greater load is applied to the foot in the state in which the user is walking than in a state in which the user remains stationary. By manufacturing the resin frame based on the foot sole form of the bare foot in the state in which the user is walking and by placing the insole pads based on the foot sole form to which the pads are applied in the state in which the user is walking, the shoe insole which is effective to the correction or the like of the sole of the foot of the user, can be manufactured.

The test pads applied to the sole of the bare foot of the user may be selected from a test pad set including a plurality of test pads which are different from each other in shape, and correspond to a plurality of specified regions of the sole of the foot to which the test pads are applied, respectively, and the insole pads applied to the upper surface of the insole frame may be selected from an insole pad set including a plurality of insole pads having the same shapes as shapes of the plurality of test pads included in the test pad set, respectively.

Since the test pad set and the insole pad set which are associated with each other are prepared in advance, and the test pads and the insole pads are selected from the test pad set and the insole pad set, the shoe insole can be manufactured easily.

Advantageous Effects of Invention

The present invention has the above-described configuration, and can achieve an advantage that a shoe insole which is appropriate for the foot of the user and is effective to the correction or the like of the sole of the foot of the user, can be manufactured in the method of manufacturing the shoe insole.

The above and further objects, features and advantages of the present invention will more fully be apparent from the following detailed description of the preferred embodiment with accompanying drawings.

BRIEF DESCRIPTION OF DRAWINGS

FIG. 2 is an exploded view of the shoe insole of FIG. 1.

DESCRIPTION OF EMBODIMENTS

Hereinafter, the preferred embodiment of the present invention will be described with reference to the drawings. Although in the embodiment, the shoe insole for a left foot will be mainly described, the same applies to the shoe insole for a right foot. The present invention is not limited to the embodiment described below.

Embodiment

Figures 1A, 1B:
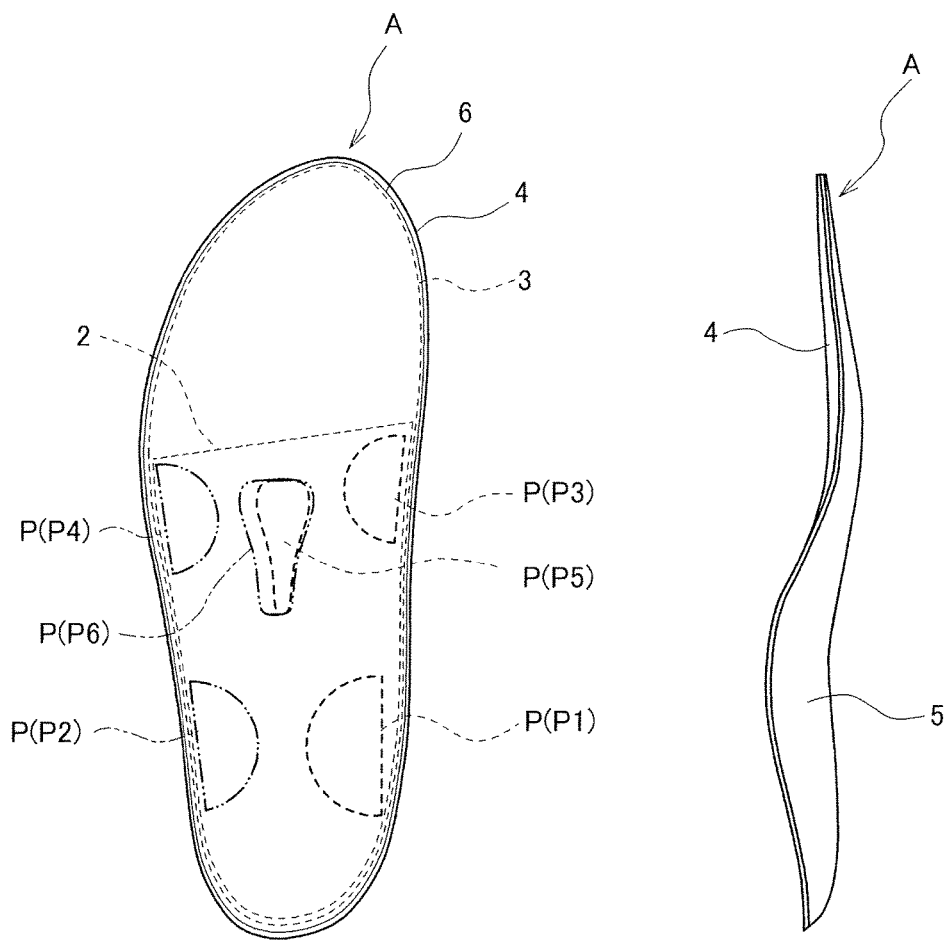
FIG. 1A is a plan view of a shoe insole for a left foot which is manufactured by a method of manufacturing a shoe insole according to the embodiment of the present invention, when viewed from above.
FIG. 1B is a side view of the shoe insole.

FIG. 1A is a plan view of the shoe insole for the left foot which is manufactured by a method of manufacturing a shoe insole according to the embodiment of the present invention, when viewed from above. FIG. 1B is a side view of the shoe insole. FIG. 2 is an exploded view of the shoe insole of FIG. 1.

As shown in FIG. 2, a shoe insole A includes an upper cover layer 4, a lower cover layer 5, and an insole body 1 retained between the upper cover layer 4 and the lower cover layer 5.

The insole body 1 includes a resin frame (insole frame) 2 having a three-dimensional shape fitted to the shape of the sole of the bare foot of a user who uses the shoe insole A, rubber insole pads P (e.g., P1, P3, P5), and a buffering layer 3 conforming in shape to the inner bottom of the shoe formed by use of the shoe insole A. In the insole body 1, the insole pads P are applied to the upper surface of the resin frame 2 and the buffering layer 3 is applied onto the upper surface of the resin frame 2 attached with the insole pads P.

The outer peripheral portion of the upper cover layer 4 and the outer peripheral portion of the lower cover layer 5 are sewn together by machine-sewing thread 6 in such a manner that the insole body 1 is covered by the upper cover layer 4 and the lower cover layer 5.

Although in the example of FIG. 1A, the examples of the regions to which the insole pads P2, P4, P6 are applied, respectively, are indicated by two-dotted lines, the insole pads P2, P4, P6 are not used for the shoe insole A.

The resin frame 2 can be formed using, for example, an ABS resin, etc. The buffering layer 3 can be formed using, for example, an EVA resin, etc. The upper cover layer 4 can be formed by, for example, a sheet of a polyester cloth, cotton pile, etc. The lower cover layer 5 can be formed by, for example, a sheet of synthetic leather, artificial leather, etc.

Figure 3:
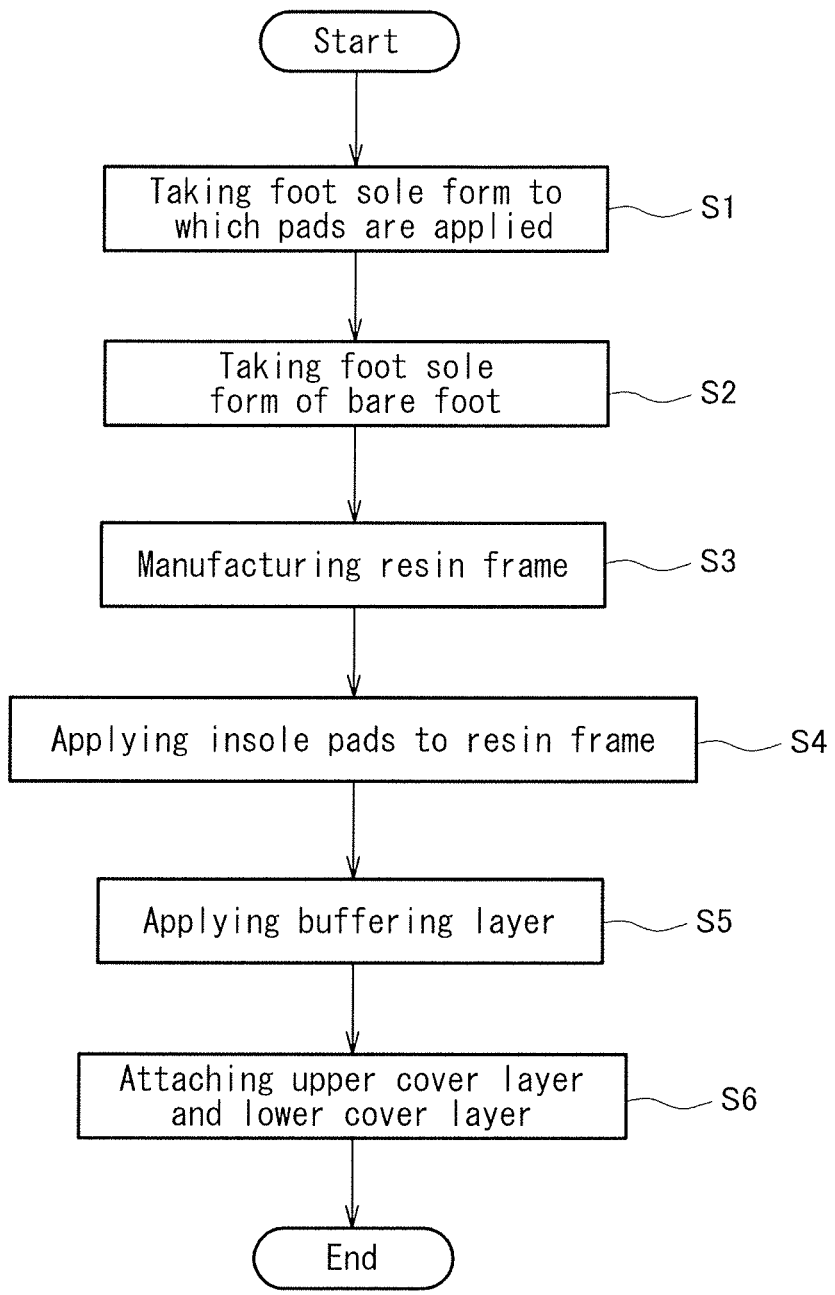
FIG. 3 is a flowchart showing an example of the method of manufacturing the shoe insole, according to the embodiment of the present invention.

Next, an example of a method of manufacturing the shoe insole according to the embodiment will be described. FIG. 3 is a flowchart showing an example of the method of manufacturing the shoe insole, according to the embodiment.

The shoe insole A is custom-made. The shoe insole A is effective to the correction or the like of the sole of the foot of the user (e.g., patient) who uses the shoe insole A. The shoe insole A is manufactured to cure deformation of toes or the like of the user, such as hallux valgus, or to facilitate the correction or the like of the standing and walking postures of the user.

To select the insole pads P (P1 to P6) used in the shoe insole of each of the right and left shoes of the user and determine the regions to which the insole pads P are attached, respectively, an evaluator such as a physical therapist or a prosthetist initially applies test pads (Ps1 to Ps6) which have the same shapes as those of the insole pads P (P1 to P6), respectively, to the sole of the foot of the user, evaluates the distortion (misalignment) or the like of the body of the user, and select the test pads Pc appropriate for the user. This will be described in detail next.

Figure 4:
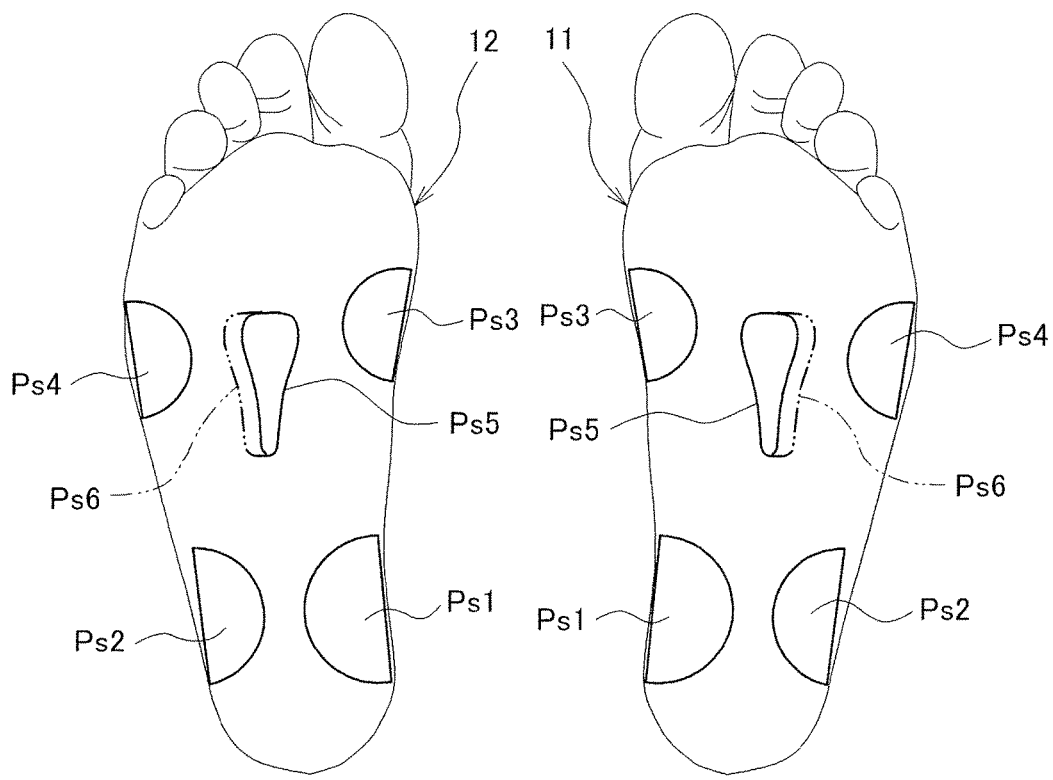
FIG. 4 is a view showing an example of test pads and regions to which the test pads are applied, respectively, according to the embodiment of the present invention.

FIG. 4 is a view showing an example of the test pads Ps (Ps1 to Ps6) and the regions to which the test pads Ps are applied.

In the present embodiment, for each of the left foot 11 and the right foot 12 of the user, the test pads Ps1 to Ps6 to be applied to a plurality of specified regions are prepared in advance. The test pads Ps1 to Ps6 have predetermined shapes conforming to the shapes of the regions to which the test pads Ps1 to Ps6 are applied, respectively.

Now, the purpose of applying the test pads Ps1 to Ps6, and an example of the regions to which the test pads Ps1 to Ps6 are applied, respectively, will be described. The insole pads P1 to P6 actually used in the shoe insole correspond to the test pads Ps1 to Ps6, respectively. The purpose of applying the insole pads P1 to P6, and an example of the regions to which the insole pads P1 to P6 are applied, respectively, are the same as those of the test pads Ps1 to Ps6.

The pad Ps1 (P1) is applied to the sole of the foot such that the center of the pad conforms to, for example, a region immediately below malleolus medialis, to facilitate guiding the pronation of a subtalar joint. The pad Ps2 (P2) is applied to the sole of the foot such that the distal end of the pad conforms to, for example, a fifth metatarsal base (base of metatarsal bone) to facilitate guiding the supination of the subtalar joint.

The pad Ps3 (P3) is applied to the sole of the foot such that the pad conforms to, for example, the outer side of a big toe sphere. The pad Ps4 (P4) is applied to the sole of the foot such that the proximal end of the pad conforms to, for example, the fifth metatarsal base, to facilitate the elevation of a little toe.

The pad Ps5 (P5) is applied to the sole of the foot such that the pad conforms to, for example, the proximal end of a metatarsal head region and second and third metatarsal regions without contacting the metatarsal head region, to raise the second and third metatarsal bones to realize a narrower transverse arch and to increase the tension of plantar fascia. The pad Ps6 (P6) is applied to the sole of the foot such that the pad conforms to, for example, the proximal end of the metatarsal head region and second, third and fourth metatarsal regions without contacting the metatarsal head region, to raise the second, third and fourth metatarsal bones to realize a wider transverse arch and to release the tension of the plantar fascia.

One (surface applied to the sole of the foot) of the surfaces of each of the test pads Ps is applied with an adhesive agent, and a paper liner is applied to this surface. The paper liner is peeled off and the test pad Ps can be applied to the sole of the foot.

The evaluator causes the user to perform forward bending in a standing posture, take a stationary standing posture, walk, etc. The evaluator selects the test pads to be appropriately applied to each of the right foot and left foot of the user. The evaluator determines the regions to which the selected test pads are applied, respectively, and applies the test pads to the determined regions, respectively. In this case, for example, the evaluator initially determines whether or not to apply the test pads Ps1, Ps2, and the regions to which the test pads Ps1, Ps2 are applied, respectively (in a case where the test pads Ps1, Ps2 are applied). Then, the evaluator determines whether or not to apply the test pads Ps3, Ps4, and the regions to which the test pads Ps3, Ps4 are applied, respectively. Lastly, the evaluator determines whether or not to apply the test pads Ps5, Ps6, and the regions to which the test pads Ps5, Ps6 are applied, respectively. However, the order in which the test pads are applied is merely exemplary.

More specifically, the evaluator initially applies the test pads Ps1, Ps2 to the user, and then causes the user to perform forward bending in a standing posture. The evaluator determines whether or not to apply the test pads Ps1, Ps2, and the regions to which the test pads Ps1, Ps2 are applied, respectively, to allow the user to bend the body to a great extent.

Then, in a state in which the test pads Ps1, Ps2 are applied to the determined regions, respectively, the evaluator applies the test pads Ps3, Ps4 to the sole of the foot and causes the user to perform forward bending in a standing posture in the same manner as that described above, take a stationary standing posture, walk, etc. The evaluator observes a balance between a right body part and a left body part (the position of a shoulder, the position of a bony pelvis, whether knees face inward or outward, whether foot arches are low or high, etc.), and determines whether or not to apply the test pads Ps3, Ps4, and the regions to which the test pads Ps3, Ps4 are applied, respectively, to make a balance between the right body part and the left body part.

Then, in a state in which the test pads Ps3, Ps4 are applied to the determined regions, respectively, the evaluator applies the test pads Ps5, Ps6 to the sole of the foot and causes the user to walk, etc. The evaluator observes a balance between the right body part and the left body part, length of stride of the right foot and the left foot, etc., and determines whether or not to apply the test pads Ps5, Ps6, and the regions to which the test pads Ps5, Ps6 are applied, respectively.

It should be noted that both of the test pads Ps5, Ps6 are not applied to one (left foot or right foot) of the feet. The same applies to the insole pads P5, P6.

In the above-described manner, the evaluator selects the test pads Ps to be applied to the sole of each of the right foot and the left foot, and determines the regions to which the test pads Ps are applied, respectively, to achieve good arches of the soles of the feet of the user and make a good balance between the right body part and the left body part.

Then, as shown in FIG. 3, in a state in which the test pads Ps determined by the evaluator are applied to the sole of each the right foot and the left foot of the user, the foot sole form (foot sole form to which the pads are applied) of each of the right foot and the left foot of the user is taken by use of a foot sole form member in the form of a foot sole form sponge (step S1).

Then, the test pads Ps are removed, and then the foot sole form of each of the right bare foot and the left bare foot of the user is taken by use of the foot sole form sponge (step S2).

Figure 5A:
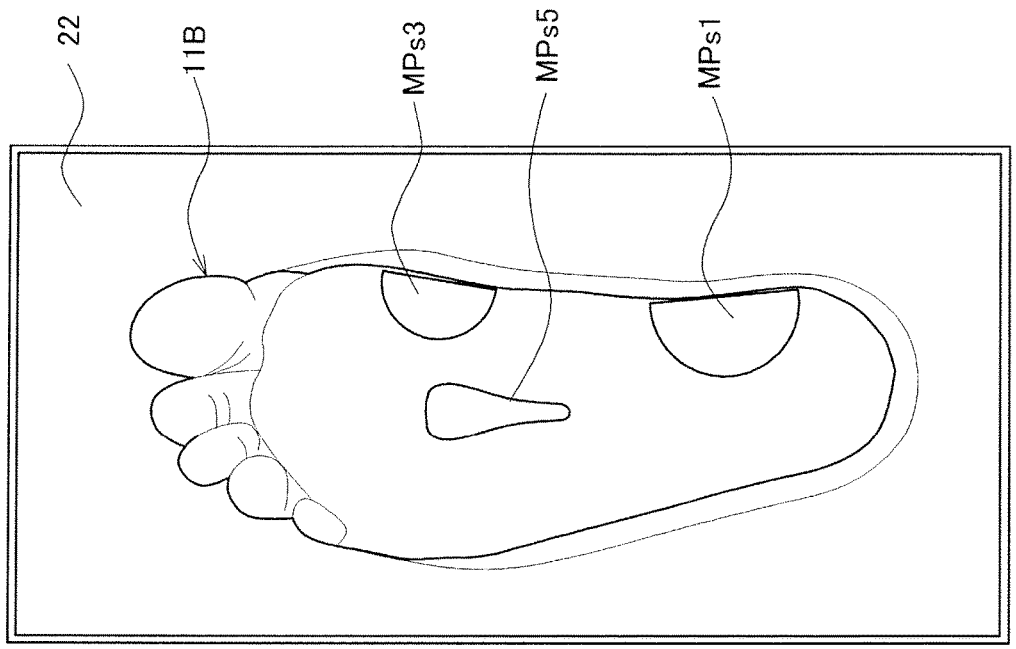
FIG. 5A is a view showing an example of a foot sole form of a bare foot which is taken by use of a foot sole form sponge.

FIG. 5A is a view showing an example of the foot sole form of the bare foot which is taken by use of a foot sole form member in the form of a foot sole form sponge 21. FIG. 5A shows a foot sole form 11A of the left bare foot. The foot sole form of the right bare foot is taken in the same manner.

Figure 5B:
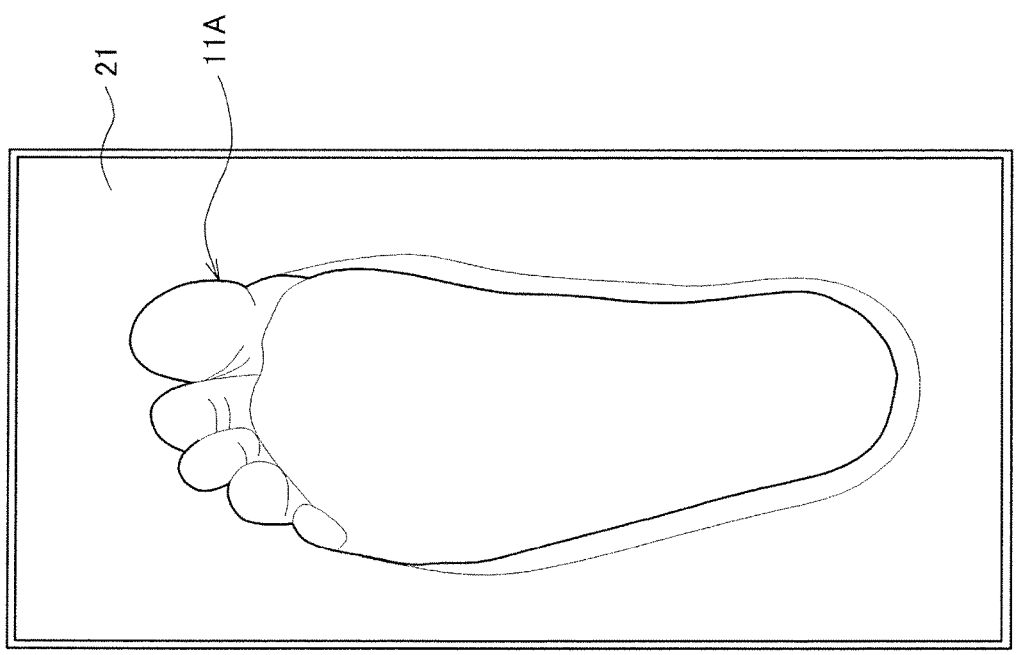
FIG. 5B is a view showing an example of a foot sole form to which pads are applied, which is taken by use of a foot sole form sponge.

FIG. 5B is a view showing an example of the foot sole form to which the pads are applied, which is taken by use of a foot sole form member in the form of a foot sole form sponge 22. FIG. 6B shows a foot sole form 11B of the left foot to which the pads are applied. MPs1, MPs3, MPs5 indicate the marks of the test pads Ps1, Ps3, Ps5, respectively, applied to the sole of the left foot. The foot sole form of the right foot to which the pads are applied is taken in the same manner.

Then, the resin frame 2 of each of the right and left insoles is manufactured based on the foot sole form of each of the right bare foot and the left bare foot (step S3). In this case, for example, the foot sole form 11A of the bare foot of the foot sole form sponge 21 of FIG. 5A is measured by a three-dimensional scanner. The measured three-dimensional data is read in a computer connected to the three-dimensional scanner. The computer executes, for example, a predetermined correction process of the three-dimensional data according to the shape of the inner bottom of the shoe, to provide a shape in which a specified region being close to tiptoes and including a region corresponding to toes (first to fifth toes) is missing, to create processed data. Based on the processed data, the form used to manufacture the resin frame is formed. By use of this form, the transparent resin frame 2 is manufactured by vacuum molding or the like, and the ABS resin, for example.

The resin frame 2 is manufactured to have a shape in which the specified region being close to the tiptoes and including the region corresponding to the toes is missing in such a way that the obverse surface (upper surface) of the resin frame 2 conforms in shape (contour) to the sole of the foot, for example, a region from a calcaneal bone to the metatarsal head region, in order to reduce a pressure to the toes, in a state in which the user is wearing the shoe. However, such a shape is merely exemplary. For example, the region of the resin frame 2, which is close to the tiptoes may be formed, so long as this region can be manufactured to be more flexible and thinner. In this case, preferably, the region corresponding to the toes is formed as a substantially flat surface.

Then, the insole pads P are applied to the upper surface of the resin frame 2 in the marks of the test pads Ps of the foot sole form to which the pads are applied, respectively (step S4). For example, the insole pads P1, P3, P5 are applied to the resin frame 2 in the positions of the marks MPs1, MPs3, MPs5 of the test pads Ps1, Ps3, Ps5 of the foot sole form 11B of FIG. 5B, respectively, to which the pads are applied. More specifically, for example, the transparent resin frame 2 is put on the foot sole form 11B to which the pads are applied, and the insole pads P1, P3, P5 are applied to the regions of the marks MPs1, MPs3, MPs5, respectively. In this way, the insole pads P1, P3, P5 can be easily applied to the resin frame 2 in correct positions, respectively. For example, the surface Pb (FIG. 2) of each of the pads P is applied with an adhesive agent, and a paper liner is applied to this surface Pb. The paper liner is peeled off and the test pads P can be applied to the resin frame 2.

Then, the buffering layer 3 conforming in shape to the inner bottom of the shoe, is applied to the upper surface of the resin frame 2 to which the insole pads P are applied (step S5). For example, the surface 3b (FIG. 2) of the buffering layer 3 is applied with an adhesive agent, and a paper liner is applied to this surface 3b. The paper liner is peeled off, and the buffering layer 3 can be applied to the resin frame 2. Thus, the insole body 1 is manufactured.

Then, the upper cover layer 4 and the lower cover layer 5 conforming in shape to the inner bottom of the shoe are attached to the insole body 1 (step S6). In the present example, the upper cover layer 4 and the lower cover layer 5 are applied to the insole body 1, and their outer peripheral portions are sewn together. Each of the surface 4b (FIG. 2) of the upper cover layer 4 and the surface 5b (FIG. 2) of the lower cover layer 5 is applied with an adhesive agent, and a paper liner is applied to each of the surface 4b and the surface 5b. The paper liner is peeled off and each of the upper cover layer 4 and the lower cover layer 5 can be applied to the insole body 1. The upper cover layer 4 is applied to the upper surface of the buffering layer 3, while the lower cover layer 5 is applied to the lower surface of the resin frame 2 and the lower surface of the buffering layer 3. The size of the buffering layer 3 is slightly smaller than those of the upper cover layer 4 and the lower cover layer 5. After the upper cover layer 4 is applied to the upper surface of the buffering layer 3, and the lower cover layer 5 is applied to the lower surface of the resin frame 2 and the lower surface of the buffering layer 3, the outer peripheral portion of the upper cover layer 4 and the outer peripheral portion of the lower cover layer 5 are sewn together by the machine-sewing thread 6. Thus, the shoe insole A is completed.

Alternatively, in the above-described steps S1 to S6, the order of the step S1 of taking the foot sole form to which the pads are applied, and the step S2 of taking the foot sole form of the bare foot may be reversed. Specifically, after taking the foot sole form of the bare foot, the evaluator may determine the test pads Ps to be applied to the sole of each of the right foot and the left foot, and the regions to which the test pads Ps are applied, respectively, and then take the foot sole form to which the pads are applied.

The insole pads P1 to P6 have the same shapes as those of the test pads Ps1 to Ps6, respectively, and are made of rubber. The test pads Ps1 to Ps6 are softer than the insole pads P1 to P6, because the user to which the test pads Ps1 to Ps6 are applied to the bare foot, walks, etc. For this reason, the test pads Ps1 to Ps6 are easily depressed by the weight of the user. In light of this, the thickness (e.g., 3 mm) of the test pads Ps1 to Ps6 is set to be slightly larger than the thickness (e.g., 2 mm) of the insole pads P1 to P6. This is merely exemplary, and the test pads Ps1 to Ps6 may be the same as the insole pads P1 to P6, respectively.

Each of the test pads Ps1 to Ps6 and the insole pads P1 to P6 has a line-symmetric shape. For this reason, for both of the right foot and the left foot, the same test pads Ps1 to Ps6, and the same insole pads P1 to P6 can be used.

Alternatively, the upper cover layer 4 and the buffering layer 3 may be integrated. For example, the buffering layer 3 may be omitted, and an upper cover layer having a function of the buffering layer 3 may be provided.

In the present embodiment, the expert (evaluator) such as the physical therapist or the prosthetist determines the regions to which the test pads Ps are applied, respectively, which are appropriate for the user. Then, based on the marks MPs (MPs1, MPs3, MPs5, etc.) of the test pads of the taken foot sole form 11B to which the pads are applied, the expert applies the insole pads P having the same shapes as those of the test pads Ps, respectively, to the upper surface of the resin frame 2. In this way, the insole pads P are placed in the positions appropriate for the user. In other words, by taking the foot sole form 11B to which the pads are applied, the insole pads P can be placed in the correct positions. This makes it possible to manufacture the shoe insole which is appropriate for the foot of the user and is effective to the correction or the like of the sole of the foot of the user.

In the present embodiment, a test pad set (six test pads Ps1 to Ps6) and the corresponding insole pad set (six insole pads P1 to P6) are prepared in advance, and the test pads Ps and the insole pads P are selected from the test pad set and the insole pad set and used. In this way, the shoe insole A can be easily manufactured.

Figure 6:
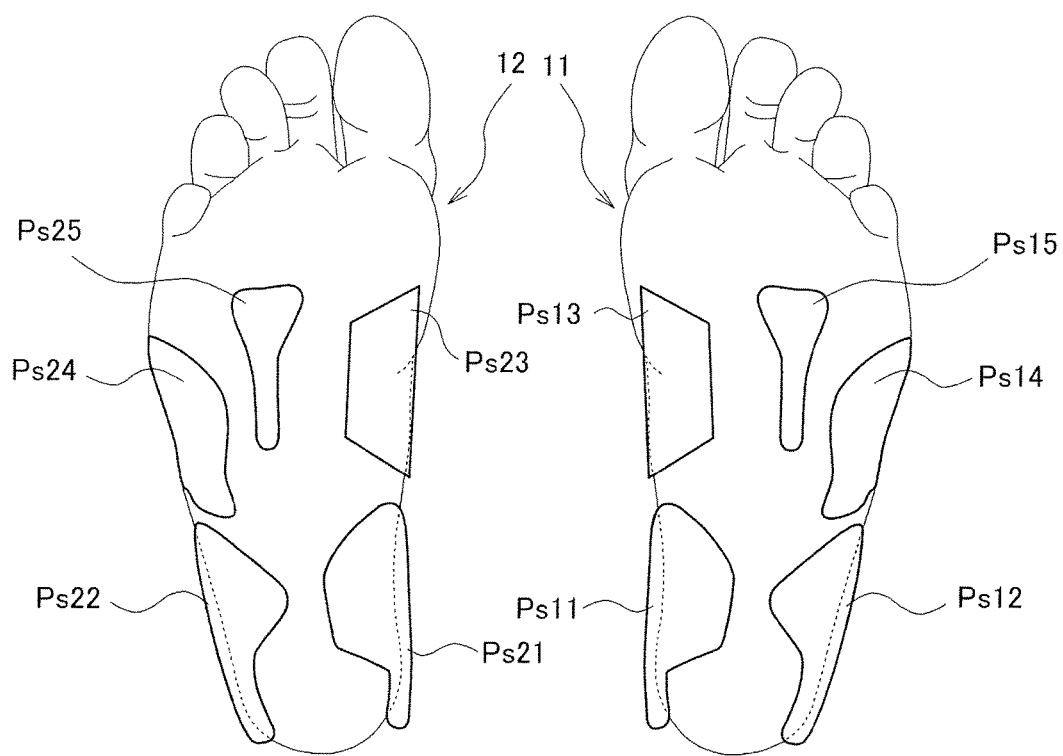
FIG. 6 is a view showing another example of the test pads and the regions to which the test pads are applied, respectively, according to the embodiment of the present invention.

The test pads Ps1 to Ps6 of FIG. 4 and the insole pads P1 to P6 of FIG. 1 are merely exemplary. They may have other shapes. Also, the regions to which the pads are applied may be changed appropriately (e.g., according to the shape of the sole of the foot of the user). For example, FIG. 6 shows another example of the test pads and the regions to which the test pads are applied, respectively. In the example of FIG. 6, test pads Ps11 to Ps15 for the left foot 11 are different (separate) from and symmetric with test pads Ps21 to Ps25 for the right foot 12, respectively. The same applies to the insole pads.

Alternatively, the test pads Ps may be formed in such a manner that desired shapes are cut out from a sheet pad material, by the evaluator, when the test pads Ps are applied to the sole of the foot. In this case, also, the insole pads P may be formed in such a manner that desired shapes which are the same as those of the test pads Ps may be cut out from the sheet pad material.

The foot sole form taken in each of the above-described steps S1 and S2 may be the foot sole form in, for example, a state in which the user is standing or is stationarily seated. Nonetheless, the foot sole form taken in each of the steps S1 and S2 is preferably the foot sole form taken by causing the user to push the foot sole form sponge with the sole of the foot and move over out of the foot sole form sponge, namely, in the state in which the user is walking. The reason is as follows. A greater load is applied to the foot in the state in which the user is walking than in the state in which the user remains stationary. By manufacturing the resin frame 2 based on the foot sole form of the bare foot in the state in which the user is walking and by placing the insole pads P based on the foot sole form to which the pads are applied in the state in which the user is walking, the shoe insole which is appropriate for the foot of the user and is effective to the correction or the like of the sole of the foot of the user, can be manufactured.

In a case where the foot sole form in the state in which the user remains stationary is taken, for example, the shape of the sole of the foot to which the test pads Ps are applied may be measured by use of a three-dimensional measurement device such as a three-dimensional scanner, to obtain three-dimensional data of the shape of the sole of the foot to which the test pads Ps are applied, without using the foot sole form sponge. In the same manner, the shape of the sole of the bare foot may be measured by use of the three-dimensional measurement device such as the three-dimensional scanner, to obtain three-dimensional data of the shape of the sole of the bare foot. In other words, the foot sole form taken in each of the above-described steps S1 and S2 of FIG. 3 may be the foot sole form comprising the three-dimensional data (three-dimensional shape data) of the shape of the sole of the foot.

Numerous modifications and alternative embodiments of the present invention will be apparent to those skilled in the art in view of the foregoing description. Accordingly, the description is to be construed as illustrative only, and is provided for the purpose of teaching those skilled in the art the best mode of carrying out the invention. The details of the structure and/or function may be varied substantially without departing from the spirit of the invention.

INDUSTRIAL APPLICABILITY

The present invention is useful as, for example, a method of manufacturing a shoe insole which can manufacture a shoe insole which is appropriate for the foot of the user and is effective to the correction or the like of the sole of the foot of the user.

REFERENCE SIGNS LIST

A shoe insole
1 insole body
2 resin frame
3 buffering layer
4 upper cover layer
5 lower cover layer
P (P1 to P6) insole pads
Ps (Ps1 to Ps6) test pads
S1 step of taking foot sole form to which pads are applied
S2 step of taking foot sole form of bare foot
S3 step of manufacturing resin frame
S4 step of applying insole pads
S5 step of applying buffering layer
S6 step of attaching upper cover layer and lower cover layer

The invention claimed is:

1. A method of manufacturing a shoe insole comprising:
providing an upper cover sheet conforming in shape to an inner bottom of a shoe, providing a lower cover sheet conforming in shape to the inner bottom of the shoe, and providing an insole body, wherein the shoe insole comprises the insole body being retained between the upper cover sheet and the lower cover sheet, the method further comprising:
taking a padded foot sole form in a first form member by applying test pads to selected regions of a sole of a bare foot of a user which uses the shoe insole and applying the bare foot of the user with the test pads applied thereto to the first form member to thereby obtain test pad marks in the padded foot sole form;
obtaining insole pads having same respective shapes as respective shapes of the test pads, the insole pads being distinct from the test pads, applying the insole pads to an upper surface of an insole frame having a shape with a surface contour that matches the bare foot of the user using the test pad marks of the padded foot sole form as a guide to place the insole pads respectively in the same locations as corresponding ones of the test pad marks,
wherein the insole body includes the insole frame to which the insole pads are applied.

2. The method of manufacturing the shoe insole according to claim 1,
the method further comprising:
taking a bare foot sole form in a second form member of the bare foot of the user; and
manufacturing the insole frame such that the insole frame has a shape conforming to a three-dimensional shape of the bare foot sole form.

3. The method of manufacturing the shoe insole according to claim 2,
wherein the first and second form members each comprise a respective foot sole form sponge, and each of the bare foot sole form and the padded foot sole form is taken by causing the user to push the respective foot sole form sponge with the sole of the foot and move over and out of the respective foot sole form sponge in a walking motion.

4. The method of manufacturing the shoe insole according to claim 1,
wherein the insole frame is manufactured to exclude a toe region,
the method further comprising:
providing a buffering layer on the upper surface of the insole frame over the insole pads, the buffering layer conforming in shape to the inner bottom of the shoe,
wherein the insole body further includes the buffering layer.

5. The method of manufacturing the shoe insole according to claim 1,
  wherein the test pads applied to the sole of the bare foot of the user are selected from a test pad set including a plurality of test pads which are different from each other in shape and correspond to a plurality of specified regions of the sole of the foot to which the test pads are applied, respectively, and
  wherein the insole pads applied to the upper surface of the insole frame are selected from an insole pad set including a plurality of insole pads having the same shapes as shapes of the plurality of test pads included in the test pad set, respectively.

6. The method of manufacturing the shoe insole according to claim 1,
  wherein the shoe insole includes the upper cover sheet, the lower cover sheet, the insole frame, and the insole pads, the insole frame and the insole pads being disposed between the upper cover sheet and the lower cover sheet, and
  wherein, in a transverse cross-sectional view of the shoe insole, an outer peripheral surface of the insole frame is located inward of the upper cover sheet and the lower cover sheet.

* * * * *